US012629260B2

(12) United States Patent
Bleistein et al.

(10) Patent No.: US 12,629,260 B2
(45) Date of Patent: May 19, 2026

(54) HEIGHT-ADJUSTABLE IMPLANT

(71) Applicant: TAURUS GMBH & CO. KG, Alzenau (DE)

(72) Inventors: Frank Bleistein, Alzenau (DE); Annette Jaques, Alzenau (DE)

(73) Assignee: TAURUS GMBH & CO. KG, Alzenau (DE)

( * ) Notice: Subject to any disclaimer, the term of this patent is extended or adjusted under 35 U.S.C. 154(b) by 345 days.

(21) Appl. No.: 18/268,825

(22) PCT Filed: Dec. 8, 2021

(86) PCT No.: PCT/EP2021/084844
§ 371 (c)(1),
(2) Date: Jun. 21, 2023

(87) PCT Pub. No.: WO2022/135940
PCT Pub. Date: Jun. 30, 2022

(65) Prior Publication Data
US 2024/0008996 A1      Jan. 11, 2024

(30) Foreign Application Priority Data

Dec. 22, 2020    (DE) ..................... 10 2020 007 873.7

(51) Int. Cl.
*A61F 2/44*          (2006.01)
*A61F 2/30*          (2006.01)
(52) U.S. Cl.
CPC .................. *A61F 2/44* (2013.01); *A61F 2/30* (2013.01); *A61F 2002/30537* (2013.01)

(58) Field of Classification Search
CPC .... A61F 2/44; A61F 2/446; A61F 2/46; A61F 2/4611; A61F 2/30
See application file for complete search history.

(56) References Cited

U.S. PATENT DOCUMENTS 8,182,535 B2    5/2012    Kraus
8,267,998 B2    9/2012    Kraus
(Continued)

FOREIGN PATENT DOCUMENTS

EP          1501453 B1    12/2005
EP          1694257 B1    8/2009
EP          2055269 B1    4/2012

OTHER PUBLICATIONS

International Search Report Dated Apr. 4, 2022 In Application PCT/EP2021/084844, 2 Pages.
(Continued)

*Primary Examiner* — Christopher J Beccia
(74) *Attorney, Agent, or Firm* — LUCAS & MERCANTI, LLP; Klaus P. Stoffel

(57) ABSTRACT

An implant, in particular for supporting the spinal column, the height of which implant can be adjusted by rotating, about an axial axis, a drive part which is supported axially with respect to a first support part and which is provided with: an external thread that interacts with an internal thread of a second support part that is axially movable with respect to the first support part but cannot be moved rotationally; and, on the axial side thereof facing the first support part, toothing that is accessible through an access that leads radially through the first support part. The implant includes a support region of the support of the drive part, the support region being located azimuthally in the region of the access and in particular radially further inwards than the toothing.

24 Claims, 10 Drawing Sheets

(56) References Cited

U.S. PATENT DOCUMENTS

| | | | |
|---|---|---|---|
| 8,568,482 B2 | 10/2013 | Kraus | |
| 2017/0079807 A1* | 3/2017 | Wallenstein | A61F 2/44 |
| 2019/0125546 A1* | 5/2019 | Refai | A61F 2/4611 |

OTHER PUBLICATIONS

English Translation of International Preliminary Report on Patentability Search Report Dated Jun. 13, 2023, 7 Pages.

* cited by examiner

200 a)

b)

a)

b)

c)

a)

336

315

310 b)

345

310 a)

b)

100e

100d

100c

100b

100a

HEIGHT-ADJUSTABLE IMPLANT

CROSS-REFERENCE TO RELATED APPLICATIONS

The present application is a 371 of International application PCT/EP2021/084844, filed Dec. 8, 2021, which claims priority of DE 10 2020 007 873.7 filed Dec. 22, 2020, the priority of these applications is hereby claimed and the applications are incorporated herein by reference.

BACKGROUND OF THE INVENTION

The invention relates to implants, in particular spinal implants, which are height-adjustable, that is to say their part that engages with the lower vertebral region can be adapted to different axial relative settings in relation to its part that engages with the upper vertebral region.

In these, the height adjustability may be implemented by rotation of a drive part, which is performed about an axial axis. The drive part is braced axially relative to a first support part and is provided with an external thread, as well as with teeth. The external thread cooperates with an internal thread of a second support part, which is axially mobile relative to the first support part but rotationally immobile. The teeth are arranged on an axial side of the drive part facing toward the first support part and are accessible through an access leading radially through the first support part.

Such implants, the height adjustability of which is almost continuous, are already known from the art, for example from EP 1 694 257 B1.

It has, however, been found that this type of height adjustability as mentioned in the introduction does not have a reliably reproducible load resistance capability. Even a refinement of EP 1 694 257 B1 by the teaching of EP 2 055 269 B1 still does not provide a satisfactory improvement in this regard. Not least for this reason, other height-adjustable implants exist on the market, in which the drive part is equipped with an internal thread and, inter alia in a manner that allows simpler access, encloses both the first support part and the second support part provided with matching external teeth as seen in a projection onto a plane orthogonal to the axial axis, likewise in the region of the regions thereof that engage in spaces between respective flanges. Such implants are described, for example, in EP 1 501 453 B1.

SUMMARY OF THE INVENTION

The object of the invention is to develop a height-adjustable implant of the type mentioned, in which the height adjustability is imparted by means of a threaded drive part that engages in a mating thread, with a view to a good combination of satisfactory compactness and load capability.

This object is achieved in respect of a device by an implant of the type mentioned in the introduction, which is essentially characterized by an azimuthal region of the access and in particular bracing region of the bracing of the drive part, which is placed radially further inward than the teeth.

Thus, in the scope of the invention it has been found that although conventional spinal implants of the type mentioned in the introduction pass static loading tests sufficiently reliably, in dynamic rotational loading tests tilting moments are however periodically generated, which lead to damage up to the extent of material fracture on the implant.

In the solution according to the invention, conversely, such tilting moments are counteracted by the bracing region of the bracing of the drive part, which is placed azimuthally (as seen in a projection onto the plane orthogonal to the axial axis) in the region of the access and radially further inward than the teeth, and an implant that is capable of resisting not only static but also dynamic loads is thereby provided.

In one preferred configuration, the bracing is carried out by means of a bridge spanning a spatial region placed between the two sides of an azimuthal boundary of the access. It should be understood that this bridge does not protrude radially into the region in which the teeth are accessible for interlocking with a radial drive shaft. Bearing forces can at least be received over a surface and then at least partially dissipated via the two azimuthal boundaries. As is explained below with reference to the figures, the serrations of the teeth of the drive part face away from the external thread of the second support part. Correspondingly, the interlocking between the teeth and rotating mating teeth when the teeth are set in rotation with respect to the rotation axis of the mating teeth is placed to the side of the external teeth, that is to say on the axial side of the access facing toward the second support part.

In one preferred configuration, an opening region of the access extends as far as an axial passage through an axial region of the first support part, through which an axial shaft coupled rotationally fixed to the drive part penetrates. This allows synergetic use of the access on the one hand to implement the height adjustability by actuation of the drive, and on the other hand to obtain access for a displacement securing device. Thus, in this context, a securing device, which passes through the opening region and secures the implant in the adapted-height state in a secure position against twisting of the drive part relative to the first support part, is provided.

In one preferred configuration, the bridge is formed by a bracing part which is separate from the first implant part. This facilitates production despite an additional component. The drive part is braced on the axial side, toward which the serration tips of its teeth face, on the bridge/the separate component. As is explained below with reference to the figures, serrations of the teeth may bear on the separate bracing part radially further inward than on the interlocking with their serration tips.

In one preferred configuration, the bracing part extends azimuthally over more than 60°, preferably more than 90°, more preferably over more than 120°, in particular more than 180° and, in particular, is formed in the shape of a ring. In this way, an even more uniform load distribution is achieved.

According to another preferred embodiment, the bracing part bears on a bearing face of the first support part, which is placed radially between the teeth and the axial passage and is formed in the plane orthogonal to the axial direction, in particular continuously and particularly in a planar fashion. This bearing face may be the axial face of a reinforcing body, facing toward the drive part, which supports while connecting to one another axial projections or axial walls of the first support part, which engage with axial projections/axial walls of the second support part. This reinforcing body may in particular be formed integrally with the first support part, and in a preferred variant may delimit the access on an axial side facing away from the drive part.

In another preferred embodiment, an annular gap is provided between the teeth and the bearing face. That is to say, the teeth of the drive part, which engage with teeth of a radial drive shaft, i.e. the serration tips of the teeth lying in the interlock region, are not involved in the bracing. This relaxes the required axial precision during the production of the implant.

Furthermore, in one preferred configuration, an axial securing device is provided, which locks the internal thread of the second support part in an axial end region of this internal thread facing toward the first support part. It may, for example, be embodied in the form of a pin penetrating radially through one of the interlocking projections/axial walls of the second support part, which protrudes into the radial extent region of the internal thread. After insertion, the pin may be connected firmly to the second support part, for example by spot welding.

In another preferred configuration, the first support part and/or the second support part may have free axial end regions, particularly in the shape of a plate, the surface extent of which as seen in cross section exceeds of each internal thread by more than 10%, preferably more than 20%, more preferably more than 40%, in particular more than 60%. These axial end regions are preferably, for example, separate parts screwed on at the end by means of a screw. This makes it possible to employ the same basic structure with the height adjustability mechanism for different applications, in that these end regions may be provided in a multiple configuration and coupled selectively.

In another preferred configuration, the first support part comprises an a protruding projection in the region of the radial access, in particular enclosing the latter, while forming by its outer contour a shaped seat, in particular formed as a rotation lock, for a complementary shape of an operating instrument. This facilitates operation because the initial coupling between the operating instrument and the first support part does not need to be carried out, for example, by screwing in.

In this context, an instrument for actuating the implant is also provided, which has a manually actuable first shaft with mating teeth for the teeth of the drive part at its proximal end.

The instrument is preferably equipped with a sleeve arrangement, through which the first radial shaft can be guided, and a second radial shaft having an axially releasable rotationally fixed coupling to the axial securing device, the axial securing device in particular also passing through the interior of the sleeve arrangement. The axial securing device may, for example, be configured in the form of a screw and is guided with the second radial shaft through the sleeve arrangement, and is screwed into an internal thread in the access, so that its proximal end screwed in as far as the axial passage can block the axial shaft.

In another preferred configuration, the sleeve arrangement comprises an outer sleeve having a shape complementary to the shaped seat of the projection at its proximal end, and an inner sleeve having a thread for screwing together with an internal thread of the access opening.

The invention furthermore provides a set comprising one or more implants according to one of the aspects above and an instrument according to one of the aspects above.

Preferably, the set comprises a plurality of implants having at least two or more different axial dimensions of the implants when adapted to their smallest adjustable height. Furthermore, the set contains at least two pairs of the axial and regional parts with a different surface extent.

In one preferred configuration, one or more of the axial end regions, screws for their application, drive part, axial extension of the drive part, comprise a central axial passage with respect to the radial direction. This serves for weight displacement of the implant.

The material is formed from a material which is in principle suitable and approved for use as an implant, preferably from a metallic material, in particular titanium or a titanium alloy.

BRIEF DESCRIPTION OF THE DRAWING

Further features, details and advantages of the invention may be found from the following description with reference to the appended figures, in which.

DETAILED DESCRIPTION OF THE INVENTION

Figure 1:
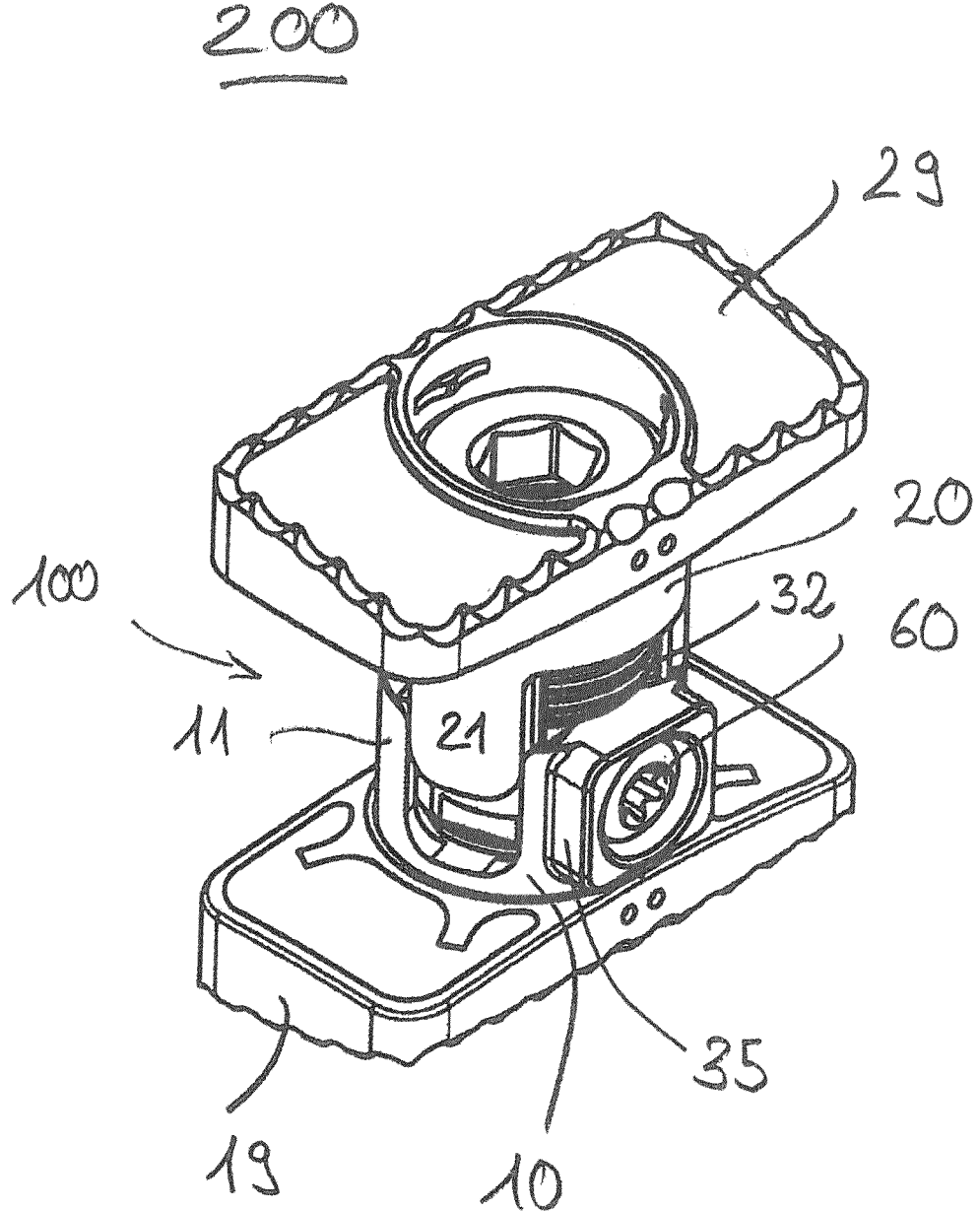
FIG. 1 shows a spinal implant in a perspective view.

FIG. 1 represents a schematic representation of a spinal implant 200, which can be inserted in a manner familiar to a person skilled in the art between two vertebrae and is used to support the spine.

In this exemplary embodiment, the implant 200 is braced on the vertebrae with plate-shaped end plates (lower end plate 19 and upper end plate 29), which are screwed together with a base unit 100. The precise shape and configuration as well as the structure of the end plates are not, however, restricted to the rectangular shape represented in the figures, and the plates may instead also have a different shape and/or structure, for instance oval or circular. The end plates may for example be provided with a structured mesh of a sintered titanium alloy.

The implant 200 is height-adjustable insofar as a lower part 10 of the base unit 100 can be displaced axially relative to an upper part 20 of the base unit 100. The displaceability comprises an axial guide, which in the present exemplary embodiment is configured by upper flange regions 21, which engage in one another with a form-fit, engaging in complementary spaces between lower flange regions 11 of the lower part 10, and vice versa, as may be seen clearly in FIG. 1.

In one preferred configuration, as in the exemplary embodiment represented, three flange regions 11 and three flange regions 21 are provided, which share the azimuthal total part of $2n$, i.e. 360°, with one another. According to a preferred but not obligatory configuration of the invention, as shown in the exemplary embodiment of FIG. 1, a flange provided with a radial access opening 14 (FIG. 3, the screw 60 blocks the opening 14 in FIG. 1) is formed with an azimuthal extent of more than 60°, and the other two lower flanges 11 and three upper flanges 21 occupy the remaining azimuthal part of the azimuthal overall circumference.

The mechanism of the height adjustability of the implant 200, or of the base unit 100 with the lower part 10 and the upper part, is carried out according to an adjustment mechanism fundamentally already familiar to a person skilled in the art, in which specifically the upper part is provided with an internal thread 22 in which the external thread 32 of a drive wheel 30 engages. If the drive wheel 30 rotates while the lower part 10 does not rotate, the upper part 21, which is axially displaceable relative to the lower part 10 but not rotatable, is displaced upward (expansion) or downward (contraction), depending on the sense of rotation.

In order to twist the drive wheel 30, it comprises a gear ring 36 (FIG. 3 and FIG. 5*a, c*), specifically on its downwardly facing axial side on the radially outer edge. In this way, the drive wheel 30 can be set in rotation by mating teeth for the teeth 36, which can be rotated about an axis of a shaft of an activation instrument. The access required for this is provided by the opening 14 (FIG. 3), the access being blocked by a locking screw 60 in the representation of FIG. 1. The locking screw 60 (FIG. 6) is inserted after the desired height of the implant 200, or of the base unit 100, has been adjusted and holds an axial extension 38 of the drive wheel 30, which is coupled rotationally fixed to the drive wheel 30, rotationally fixed by screw clamping relative to the lower part 10.

The lower part 10 comprises a reinforcing region 18, as in this exemplary embodiment preferably formed here integrally with the flange regions 11, which adjoins the flange regions 11 inward as seen radially and therefore allows the flanges 21 of the second part to be able to be displaced unimpeded axially past it. Furthermore, the reinforcing region 18 extends as seen radially into the region in which the teeth 36 of the drive wheel 30 also lie.

In order to also provide an axial access possibility for establishing the interlock with the rotating drives of the drive wheel 30, besides the radial accessibility for guiding the mating teeth through, the reinforcing region 18 comprises a recess, which is substantially U-shaped in this exemplary embodiment, specifically in the region of the access opening 14 as seen azimuthally. In the radial region of the teeth 36, the reinforcing region 18 formed here integrally with the first part therefore comprises a boundary of the substantially U-shaped cutout in the form of axial sides 15l and 15r and a bottom 13.

Radially close thereto but inside this radial region of the teeth 36, the intermediate space between the sides 15l and 15r is bridged by an annular segment 54 of a ring body 50. The ring body 50 in this case bears on an annular segment-shaped bearing region of an axial side 16 of the reinforcing region 18, which extends azimuthally between the sides 15l and 15r on the side facing away from the access opening 14.

Figure 4:
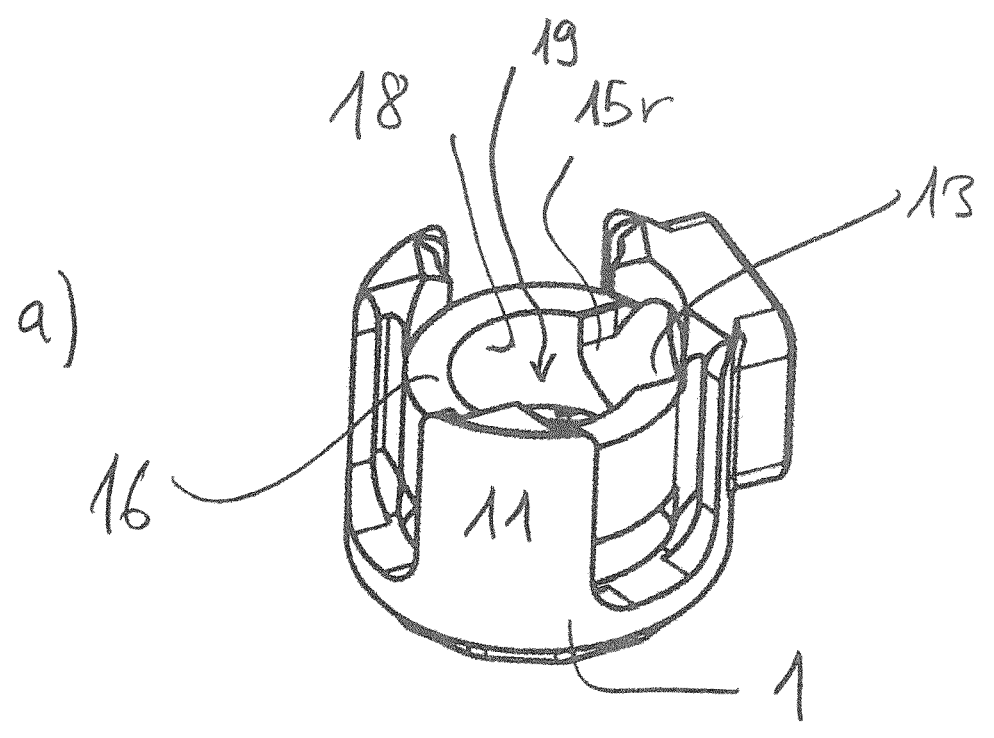
FIG. 4 shows schematic perspective representations of a region of an axial side of a lower part of the base unit of the spinal implant from two different viewing angles.
Figure 4:
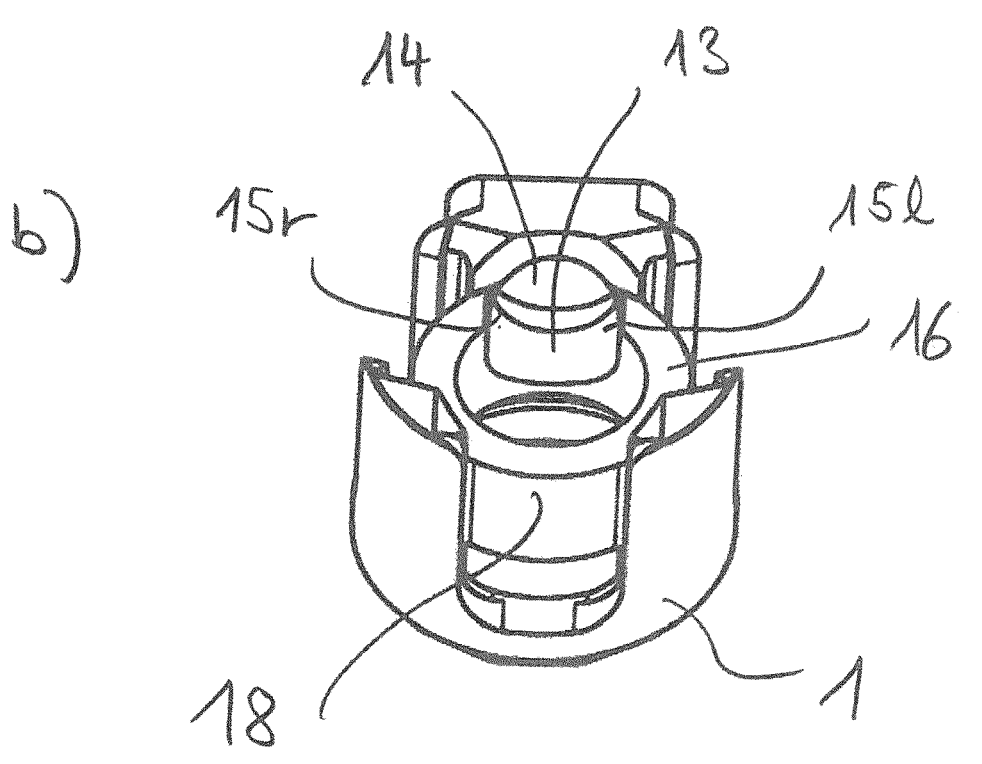
Figure 5:
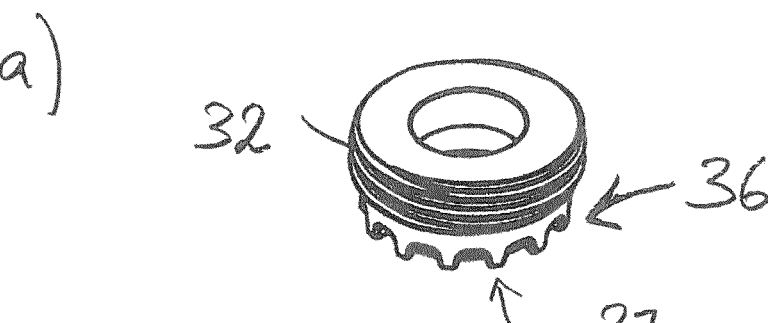
FIG. 5 shows a part of the drive with an external thread and teeth for interlocking, which initiates a height adjustment, a) obliquely from above, b) obliquely from below without and c) with a bracing force absorber.
Figure 5:
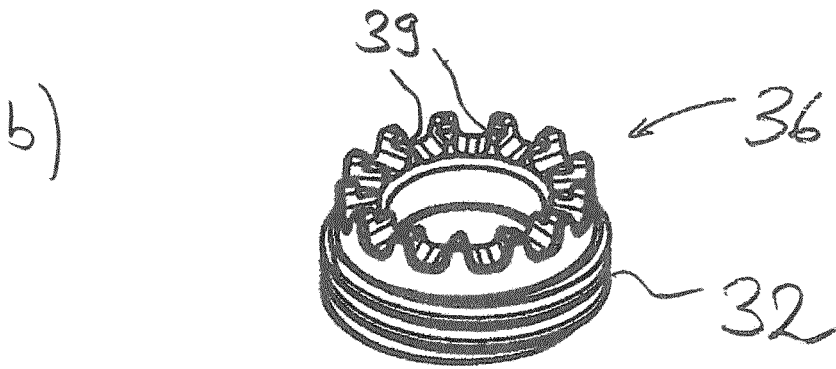
Figure 5:
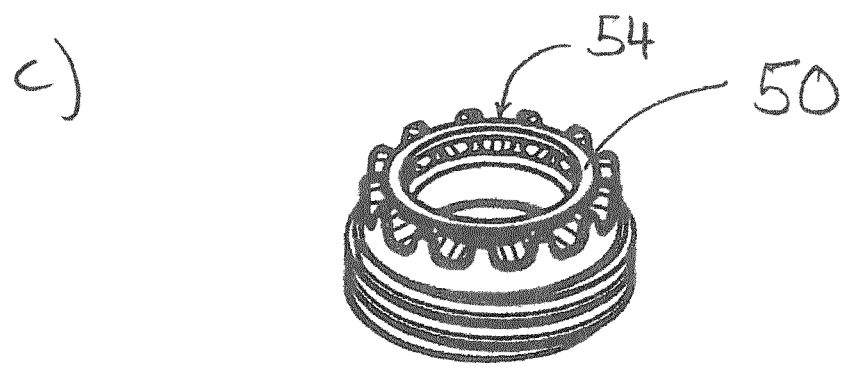
Figure 6:
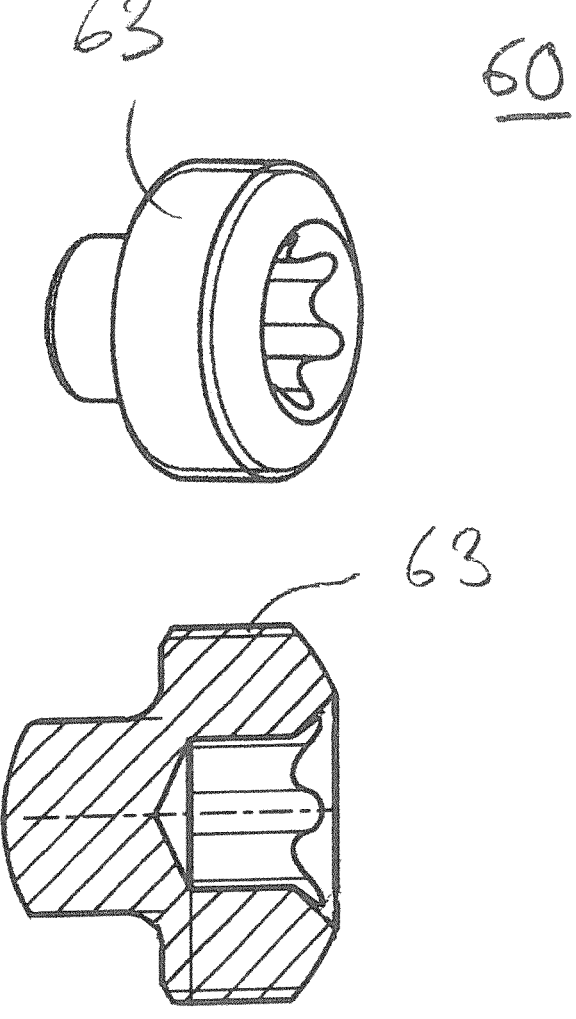
FIG. 6 shows a locking screw for securing an adjusted implant height.

In FIGS. 4*a* and 4*b*, it can be seen even more clearly that, with the ring 50 placed on, the circular segment-shaped region 54 of the ring 50 (FIG. 5*b* tilted through 180° (top to bottom) "placed" on the bearing 16 in the placement of FIG. 4*b*)) will span the opening in the manner of a bridge while connecting the azimuthal boundaries 15l and 15r of the opening 14. FIG. 5 again represents the teeth 36 in a plurality of views, also from below. In the representation of FIG. 5*c*, in comparison with the representation of FIG. 5*b*, the ring 50 is also represented. It may be seen that the teeth placed radially outward for the interlock are also generated with a larger radial extent during production and then the serration height is reduced radially inward while forming a discontinuous bearing face 39 for the ring 50.

Figure 3:
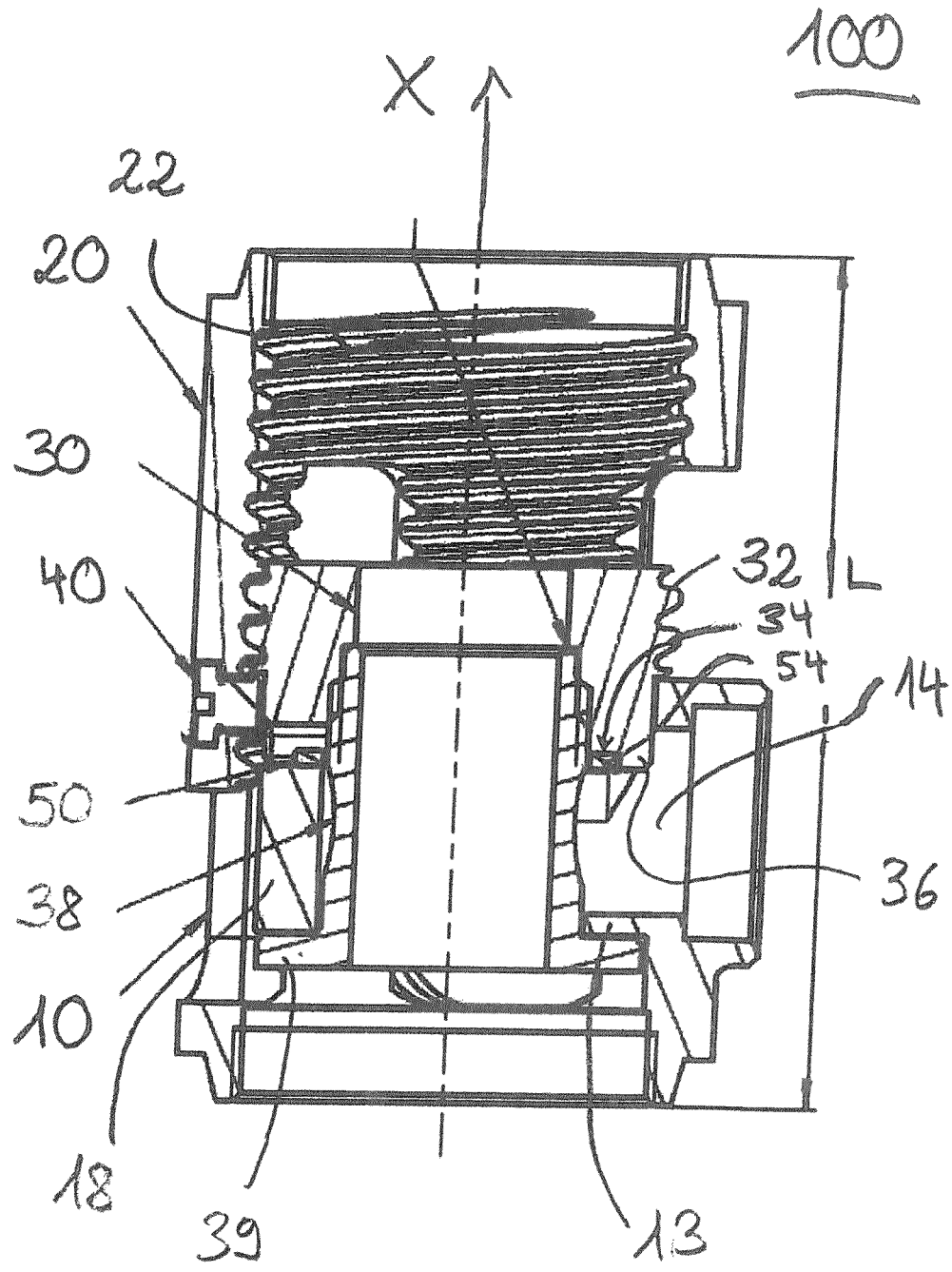
FIG. 3 shows a simplified view, partially represented in axial section, of a base unit of the spinal implant.

As may be seen from FIG. 3, the drive wheel 30 is braced axially on the reinforcing region 18 of the lower part 10 by means of the ring 50 comprising the bridge 54.

Furthermore, the axial height of the ring 50 is dimensioned so that the serration tips 37 (FIG. 5*a*) of the teeth 36 themselves, at least in the preferred configuration and also as represented in the exemplary embodiment, no longer bear on the face 16. This means that a gap is provided between the serration tips 37 of the teeth 36 and the bearing 16. Accordingly, the dissipation of the bracing force of the bracing of the drive wheel 30 into the lower part 10 takes place indirectly via the ring 50 and azimuthally also in the region of the opening 14.

In one preferred configuration, at least the bridge region 54 is provided in the form of a component which is separate from the reinforcing region 18, and more preferably, as represented best for example in FIG. 4, in the form of a closed ring body, which is provided overall as an independent component.

Figure 2:
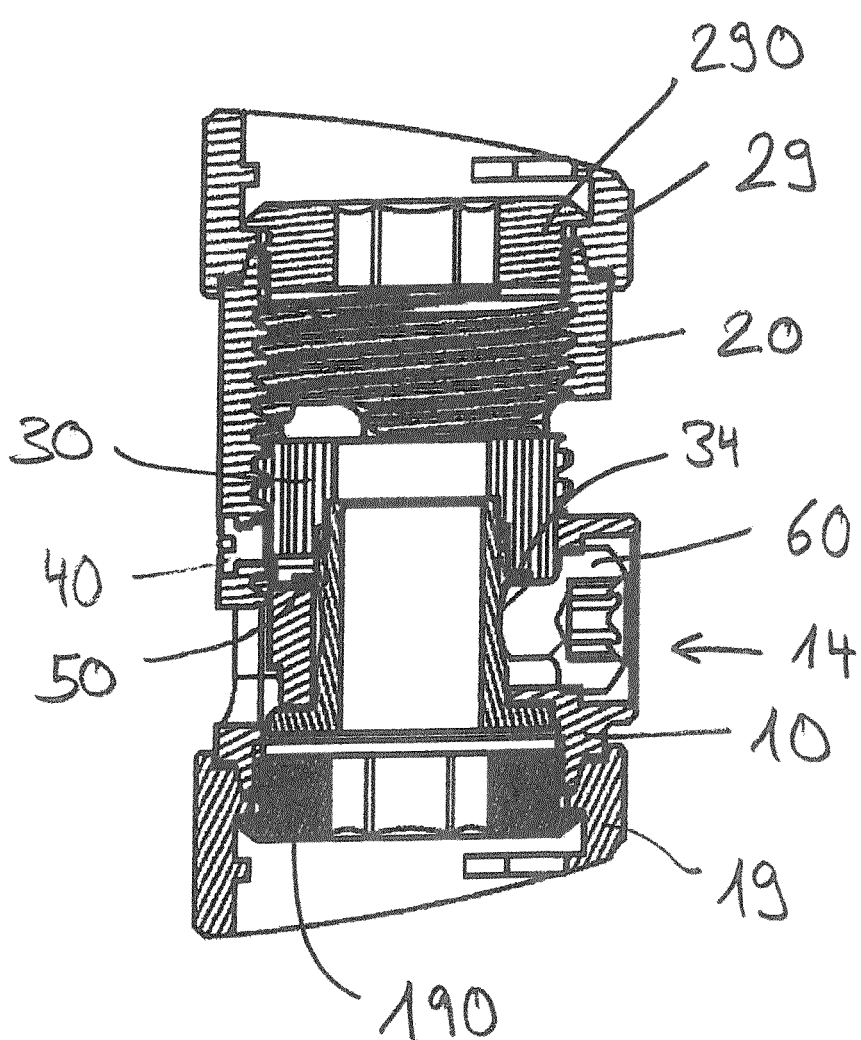
FIG. 2 is a representation of the spinal implant, partially in axial section.

As may furthermore be seen in particular from FIG. 2 and FIG. 3, a pin 40, which in this exemplary embodiment is provided in the diametrically opposite position to the access opening 14 in the lower end region of the internal teeth 22 and penetrates through this internal thread 22, ensures an axial stopper, or abutment, which prevents further twisting of the thread and therefore determines the maximum extraction of the base unit 100. The pin 40 therefore simultaneously provides security against loss.

As may be seen from FIG. 1, the interface between the lower flanges 11 and the upper flanges 21 does not run flat but has a step as seen in cross section, so that the upper flanges 21 are held in a dovetail fashion in the intermediate spaces between the lower flanges 11.

The reinforcing region 18 is, as already mentioned, essentially configured in the shape of a ring and has an axial passage 19 through which the axial continuation 38, formed as a sleeve screw, of the drive wheel 30 carrying the external thread 32 penetrates. At its free end facing away from the drive wheel 30, this continuation 38 comprises a flange region 39, so that the unit rotated with the drive wheel 30 during the height adjustment encloses the reinforcing region 38 as seen axially and overall has a radially central cavity over at least a major part of its length or even, as represented in the preferred exemplary embodiment, over its entire axial length. The fastening screws 190, 290 for the end plates 19 and 29, respectively, are also preferably formed with a central cavity as seen radially. In order to receive the fastening screws 190, 290, the first part 10 and the second part 20 respectively have at their free end an internal thread cooperating with the thread of these screws.

The shape of the internal thread 22 as seen in axial section has a substantially planar flank facing toward the free end of the upper part 20 substantially in the plane orthogonal to the axial axis X, and a flank running obliquely with respect to this plane and facing away from this free end. The pitch angle of the thread is in this exemplary embodiment about 1.75°.

As may be seen from FIG. 1, a projection 35 in the form of a circumferential wall structure, the outer contour of which forms a shaped seat for the set instrument described below, is formed on the lower flange 11 with the access opening 14. This shaped seat is formed in this exemplary embodiment by a rectangular base shape with rounded corners. The inner wall region of the projection 35 carries an internal thread, which cooperates with a thread on the free end of a further part of the set instrument (see below).

Furthermore, the access opening 14 also has an internal thread lying radially further inward, which cooperates with an external thread of the locking screw. The locking screw 60 is graphically represented again separately in a perspective view in FIG. 6. A screw head drive may be seen, in this exemplary embodiment gate-like with π/3 rotational symmetry (it should be understood that any other screw head drives may be envisioned), for coupling a part of a set instrument (see below) to the head of the locking screw, as well as a convex configuration of the distal free end face of the screw for flat contact with the concave configuration, which can be seen in FIG. 2, of the axial continuation 38 in a region at the height of the guide opening 14. The external thread of the locking screw 60 is denoted by the reference 63.

FIGS. 7a to 7f show parts of a multi-part set instrument 300, which cooperates with the implant according to the invention.

Figure 7:
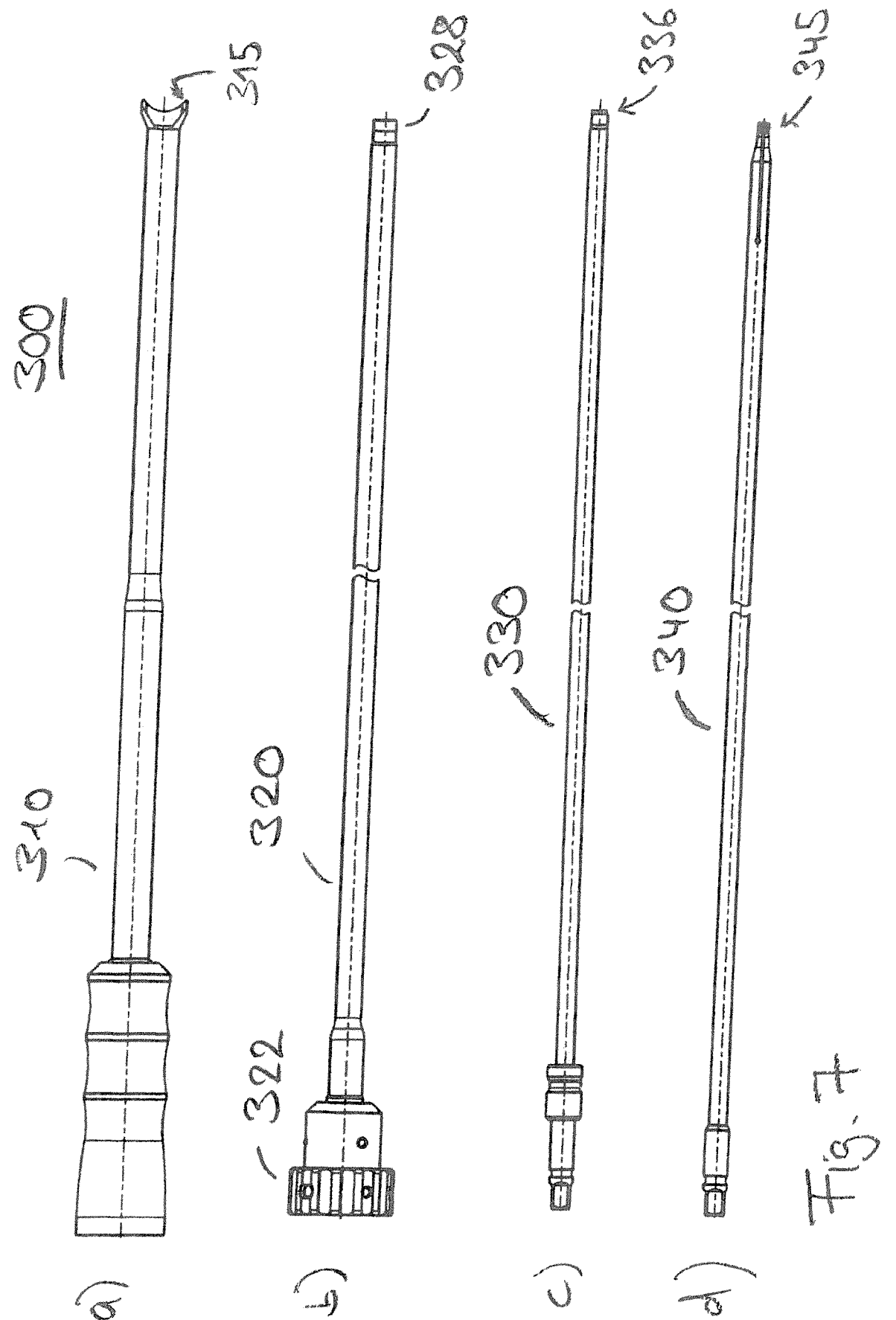
FIG. 7 shows component parts of a set instrument for the implant.

FIG. 7a) shows a view of an outer sleeve 310, at the proximal operative end of which a seat 315 that acts with a form-fit with the seat 35 of the implant is formed. The outer sleeve 310 is fitted onto the seat 35 on the implant. The inner sleeve 320 represented in FIG. 7b can be guided through this outer sleeve 310. At its operative proximal end, this inner sleeve has an external thread 328 that cooperates with the internal thread in the inner boundary of the projection 35. At the distal end, a gripping ring provided with gripping grooves protrudes radially beyond the outer sleeve and engages over the distal end of the outer sleeve.

The distal ends of the shafts 330 and 340 are used for placement of a further part (not graphically represented) of the set instrument, a palm grip with a torque limiter.

Differently configured shafts may be guided inside the inner sleeve, on the one hand the distraction shaft 330 shown in FIG. 3c, at the proximal operative end of which teeth are formed, namely mating teeth 336 for the teeth 36, and on the other hand in another operating state a locking shaft 340, which is shown in FIG. 7d, equipped at the operative proximal end with a suitable coupling 345 for screwing in the locking screw 60.

Figure 8:
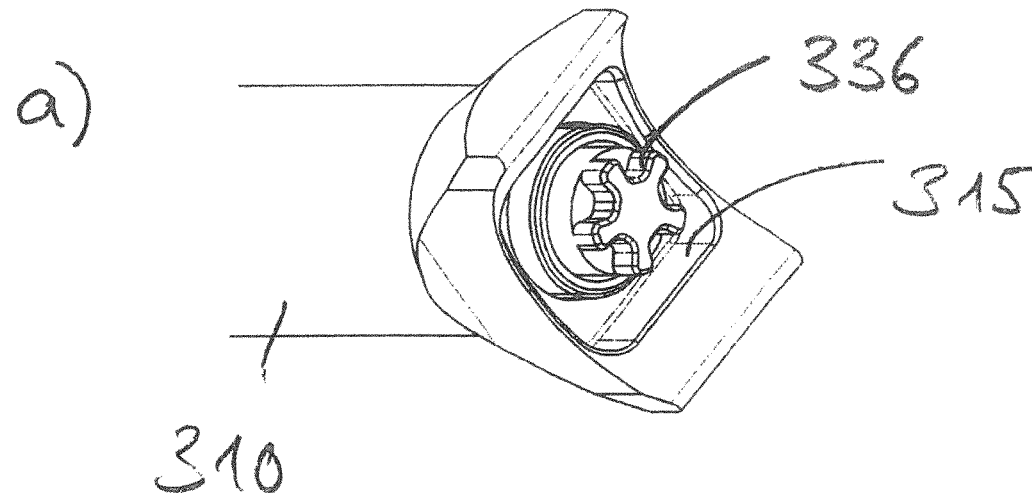
FIG. 8 shows their coupling end in two different operating states.
Figure 8:
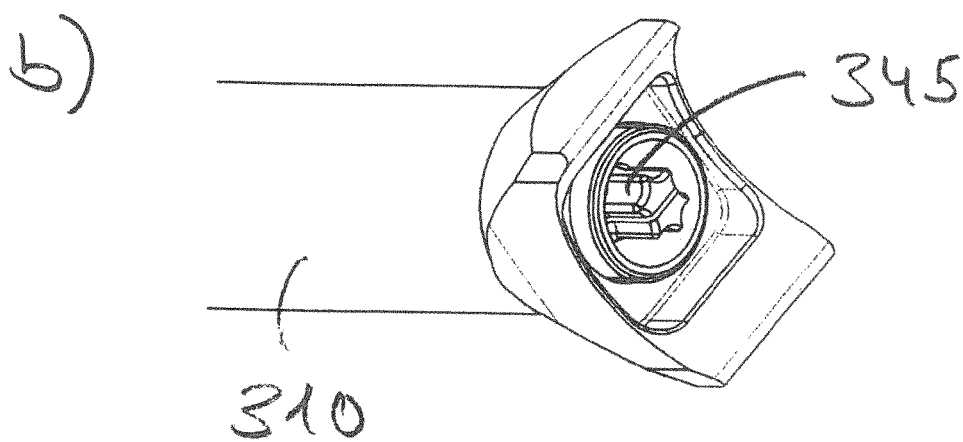

The mating teeth 336 may again be seen in FIG. 8a in an enlarged representation, in which the set instrument is represented in the first operating state with a distraction shaft guided in with its proximal end region. FIG. 8b, conversely, shows the coupling 345 that matches the inner configuration of the screw head of the locking screw 60. Both representations also show the external thread of the inner sleeve 320, with which the set instrument is temporarily screwed together with the implant. The inner sleeve 320 cooperates with the outer sleeve 310 in such a way that automatic centering of the external thread 328 with the internal thread takes place when establishing the form-fit between the mating seat 315 for the seat 35.

Figure 9:
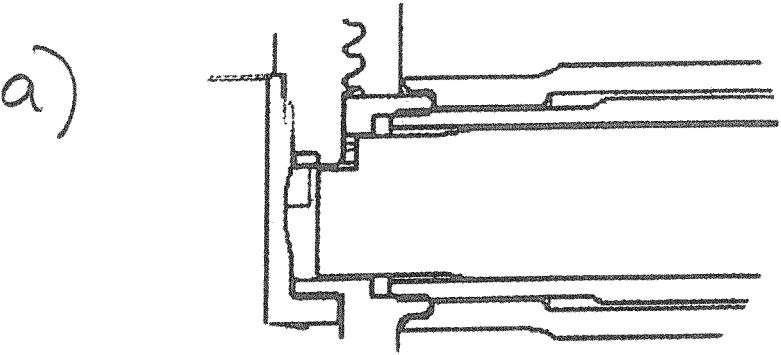
FIG. 9 shows the coupling of an implant and set instrument in two different operating states.
Figure 9:
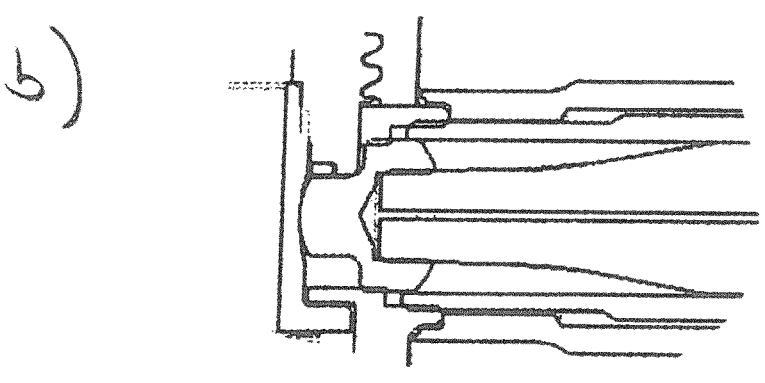

If in the first operating state the distraction shaft 330 (FIG. 7c) is guided into the inner sleeve 320, it comes to lie by radial correspondence radially at the height of the teeth 36 (FIG. 9a). Rotation of the distraction shaft 330 with interlocking of the engaging teeth pair 36-336 about the shaft axis running radially with respect to the axial axis X of the implant rotates the drive wheel 30 and via the threaded coupling 32-22 displaces the upper part 20 axially in relation to the lower part 10.

Once the desired axial height of the implant has been adjusted in this way, instead of the distraction shaft 330 the locking shaft 340, which already has the locking screw 60 fitted on, is inserted into the inner sleeve 320 (second operating state), and the locking screw 60 guided through the inner sleeve 320 is screwed in and fixes the rotational placement of the drive ring 30 and the lower part 10 (FIG. 2, 9b).

The axial coupling face of the locking screw 60 in relation to the radial axis may be configured convexly, as is done here, in order to bear with an annularly circumferential concavity of the axial continuation 38 of the drive ring 30 with a larger surface contact than only point touching as considered without forces.

Figure 10:
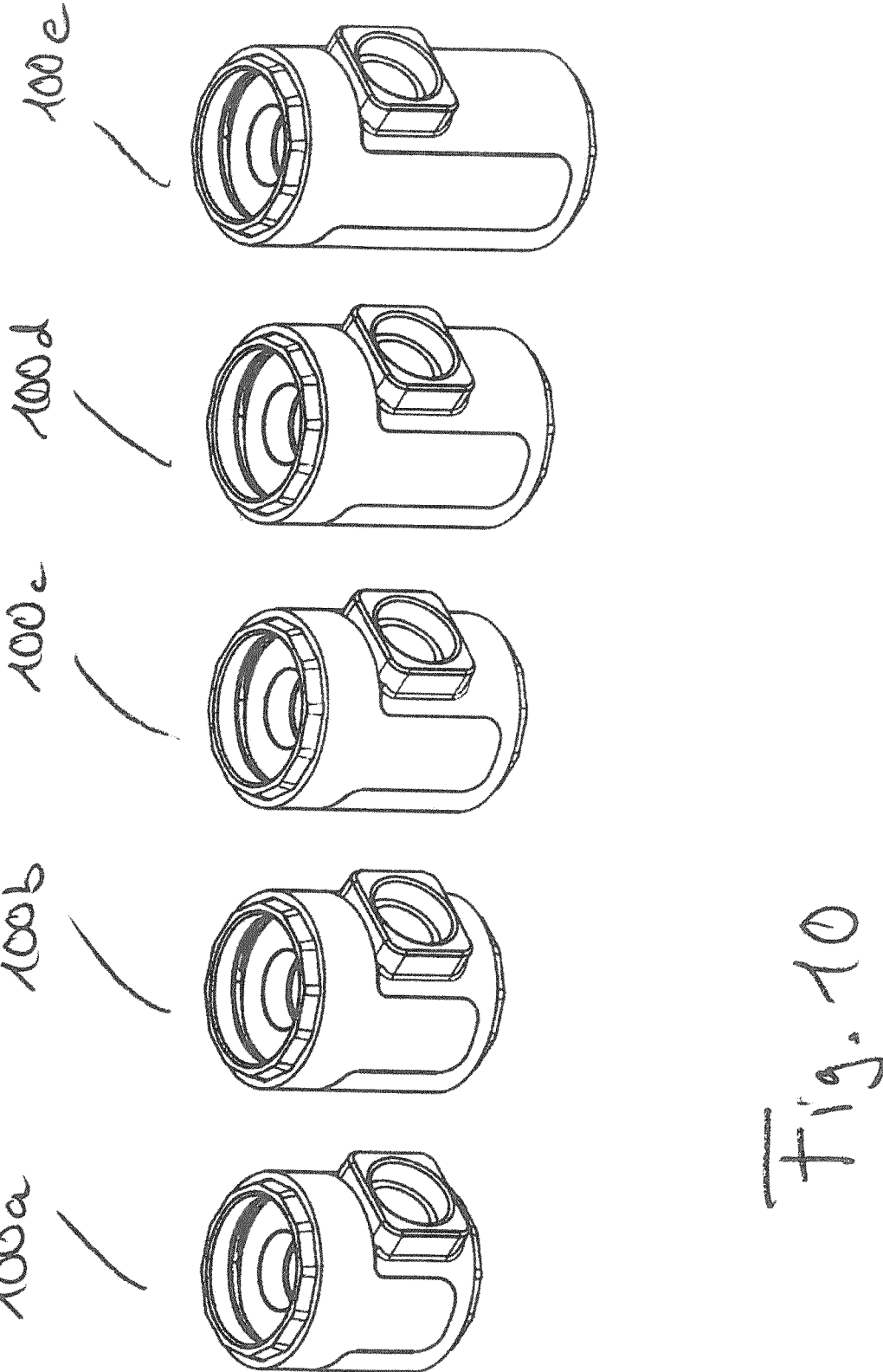
FIG. 10 shows a set of spinal implants with a different axial minimum height.

FIG. 10 represents a further plurality of base bodies 100a, 100b, 100c, 100d and 100e, which impart an even greater variability of use to a spinal implant set according to the invention. It may be seen that the implants have a different axial extent in their (neutral) state of least axial extent. The flange regions of the first and second parts are for this purpose configured with respectively increasing length, the position of the access with respect to the free end of the flange assigned thereto being the same. It should be understood that the set is not restricted to a configuration with five different implant heights, and there could also be a different number, and the height gradation respectively provided between one another is also not restricted to that represented.

Likewise, the invention is also not restricted in other regards to the details represented with the aid of the preferred exemplary embodiments. Rather, the individual features of the description above and the claims which follow may be essential individually and in combination for the implementation of the invention in its various embodiments.

The invention claimed is:

1. An implant that is height adjustable by rotation about an axial axis, in particular for supporting the spine, comprising: a first support part; a second support part that is axially mobile relative to the first support part but rotationally immobile, the second support part having an internal thread: and a drive part braced axially relative to the first support part and having an external thread that cooperates with the internal thread of the second support part, and on an axial side facing toward the first support part having teeth that are accessible through an access leading radially through the first support part, wherein the drive part is braced by a bridge that spans, azimuthally with respect to the axial axis, a spatial region placed between two sides of the access, and wherein the implant further comprises a bracing region, which is placed azimuthally in a region of the access, and, with respect to the axial axis, radially further inward than the teeth, and which comprises the bridge.

2. The implant according to claim 1, wherein an opening region of the access extends as far as an axial passage through an axial region of the first support part, through which an axial extension coupled rotationally fixed to the drive part penetrates.

3. The implant according to claim 2, further comprising a securing device that passes through the opening region and secures the implant in an adjusted-height state in a secure position against twisting of the drive part relative to the first support part.

4. The implant according to claim 2, wherein the bridge is formed by a bracing part that is separate from the first implant part.

5. The implant according to claim 4, wherein the bracing part extends azimuthally over more than 60°.

6. The implant according to claim 5, wherein the bracing part extends azimuthally over more than 120°.

7. The implant according to claim 6, wherein the bracing part extends azimuthally over more than 180°.

8. The implant according to claim 5, wherein the bracing part is formed as a ring.

9. The implant according to claim 4, wherein the bracing part bears on a bearing of the first support part, the bearing being arranged radially between the teeth and the axial passage and being formed in a plane orthogonal to the axial direction.

10. The implant according to claim 9, having an annular gap between the teeth and the bearing.

11. The implant according to claim 1, further comprising an axial securing device that locks the internal thread in an axial end region, facing toward the first support part, of the internal thread of the second support part.

12. The implant according to claim 1, wherein the first support part and/or the second support part have free axial end regions with a surface extent that, as seen in cross section, exceeds that of the internal thread by more than 10%.

13. The implant according to claim 12, wherein the surface extent of the free axial end regions exceeds that of the internal thread by more than 20%.

14. The implant according to claim 13, wherein the surface extent of the free axial end regions exceeds that of the internal thread by more than 40%.

15. The implant according to claim 14, wherein the surface extent of the free axial end regions exceeds that of the internal thread by more than 60%.

16. The implant according to claim 12, wherein the free axial end regions are plate-shaped.

17. The implant according to claim 12, wherein the free axial end regions are independent components that are screwed on.

18. The implant according to claim 1, wherein the first support part comprises a protruding projection in a region of the radial access, the protruding projection having an outer contour that forms a shaped seat for a complementary shape of an operating instrument.

19. The implant according to claim 18, wherein the protruding projection is enclosed by the radial access.

20. The implant according to claim 18, wherein the shaped seat is formed as a rotation lock.

21. An instrument for actuating an implant according to claim 1, comprising a manually actuable first shaft having a proximal end with mating teeth for the teeth of the drive part, further comprising a sleeve arrangement, through which the first shaft is guidable, and a second radial shaft having an axially releasable rotationally fixed coupling to and axial securing device, the axial securing device also passing through the interior of the sleeve arrangement.

22. The instrument according to claim 21, wherein the sleeve arrangement comprises an outer sleeve having a proximal and with a shape complementary to a shaped seat of a projection of the first support part, and an inner sleeve having a thread for screwing together with an internal thread of the access.

23. A set comprising: an implant according to claim 1; and an instrument comprising a manually actuable first shaft having a proximal end with mating teeth for the teeth of the drive part.

24. The set according to claim 23, comprising a plurality of implants having at least two or more different axial dimensions of the implants when adjusted to their smallest adjustable height.

* * * * *